(12) United States Patent
Daigle et al.

(10) Patent No.: US 8,691,292 B2
(45) Date of Patent: Apr. 8, 2014

(54) DISINFECTANT FORMULATION

(75) Inventors: François Daigle, Canton de Hatley (CA); Ann Letellier, Saint-Hyacinthe (CA); Sylvain Quessy, Sainte-Anne-de-Sorel (CA)

(73) Assignee: Laboratoire M2, Sherbrooke (CA)

( * ) Notice: Subject to any disclaimer, the term of this patent is extended or adjusted under 35 U.S.C. 154(b) by 597 days.

(21) Appl. No.: 12/420,688

(22) Filed: Apr. 8, 2009

(65) Prior Publication Data

US 2010/0034907 A1 Feb. 11, 2010

Related U.S. Application Data

(60) Provisional application No. 61/043,317, filed on Apr. 8, 2008.

(51) Int. Cl.
*A61K 36/00* (2006.01)

(52) U.S. Cl.
USPC .......................................................... 424/725

(58) Field of Classification Search
None
See application file for complete search history.

(56) References Cited

U.S. PATENT DOCUMENTS

| 3,947,570 | A | * | 3/1976 | Pensak et al. | 424/54 |
| 3,983,252 | A | * | 9/1976 | Buchalter | 514/698 |
| 4,414,128 | A | | 11/1983 | Goffinet | 252/111 |
| 5,403,587 | A | * | 4/1995 | McCue et al. | 424/736 |
| 2005/0153857 | A1 | * | 7/2005 | Sherry et al. | 510/295 |
| 2005/0182142 | A1 | * | 8/2005 | Kobayashi et al. | 514/688 |
| 2006/0210593 | A1 | * | 9/2006 | Kobayashi et al. | 424/401 |

FOREIGN PATENT DOCUMENTS

| CA | 2371925 | 12/2000 |
| CA | 2441730 | 10/2002 |
| JP | 2003012411 | 1/2003 |
| JP | 2003531246 | 10/2003 |
| JP | 2002511391 | 4/2004 |
| WO | WO 01/84936 | 11/2001 |
| WO | WO 03/037270 | 5/2003 |
| WO | WO 2007/133934 | 11/2007 |

OTHER PUBLICATIONS

Stephen E Kintzios (Oregano: the genera Origanum and Lippa, CRC Press, Aug. 20, 2002, health and fitness, p. 277).*
Kintios (Oregano: the genera Origanum and Lippa, CRC Press, Aug. 2002, Health and Fitness, p. 277).*
PCT International Search Report, issued in International applicant No. PCT/CA2009/000458, dated Jul. 13, 2009.

* cited by examiner

*Primary Examiner* — Terry A McKelvey
*Assistant Examiner* — Randall Winston
(74) *Attorney, Agent, or Firm* — Benoît & Côté Inc.

(57) ABSTRACT

An aqueous disinfectant formulation comprising at least one phenolic compound of natural origin; a surfactant sufficient to form a solution or dispersion of the essential oil in an aqueous carrier; a solvent, and sufficient water to make 100 weight percent is described herein.

20 Claims, No Drawings

DISINFECTANT FORMULATION

CROSS REFERENCE TO RELATED APPLICATIONS

The present application claims the benefit of U.S. Provisional Application No. 61/043,317 filed on Apr. 8, 2008, the entire contents of which are incorporated by reference.

FIELD OF THE INVENTION

The present invention broadly relates to disinfectant formulations comprising one or more phenolic compounds of natural origin. More specifically, but not exclusively, the present invention relates to formulations comprising one or more essential oils enriched in one or more phenolic compounds of natural origin suitable for disinfecting and cleaning large surface areas such as commonly encountered in agricultural settings, the formulations typically comprising one or more essential oils.

BACKGROUND OF THE INVENTION

In spite of modern improvements in hygiene and infection prevention, livestock health has become an increasingly important public health issue. This has been due in part to the fact that infections caused by viruses and fungi have increased as a result of travel and global interconnections.

Pathogens such as bacteria, fungi, viruses, and bacterial spores are responsible for a plethora of human and animal ills, as well as contamination of food and biological and environmental samples. The first step in microbial infections of animals is generally attachment or colonization of skin or mucus membranes, followed by subsequent invasion and dissemination of the infectious microbe. The portals of entry of pathogenic bacteria are predominantly the skin and mucus membranes.

Virtually every intensive livestock producer accepts that effective disease prevention is key for maintaining a healthy enterprise. Over the years the improvement in and availability of vaccines has greatly assisted in the prevention of a large number of diseases. However, even a well vaccinated livestock can succumb under severe challenge. Moreover, since vaccines are not available for all the diseases to be prevented, producers have accepted that a well planned and monitored bio-security program, coupled with an effective disinfection and vaccination program, is essential for maintaining the health of their stock.

Avian influenza is an infectious disease of birds caused by type A strains of the influenza virus. The disease, which was first identified in Italy more than 100 years ago, occurs worldwide. All birds are thought to be susceptible to infection with avian influenza, though some species are more resistant to infection than others. Domestic poultry, including chickens and turkeys are particularly susceptible to epidemics of rapidly fatal influenza.

Fifteen subtypes of influenza virus are known to infect birds, thus providing an extensive reservoir of influenza viruses potentially circulating in bird populations. To date, all outbreaks of the highly pathogenic form have been caused by influenza A viruses of subtypes H5 and H7. Recent research has shown that that viruses of low pathogenicity can, after circulating for sometimes short periods in a poultry population, mutate into highly pathogenic viruses.

The quarantining of infected farms and destruction of infected or potentially exposed flocks are standard control measures aimed at preventing spread to other farms and eventual establishment of the virus in a country's poultry population. Apart from being highly contagious, avian influenza viruses are readily transmitted from farm to farm by mechanical means, such as by contaminated equipment, vehicles, feed, cages, or clothing. Stringent sanitary measures on farms can, however, confer some degree of protection.

A great many of the current antimicrobial compositions, including sanitizers and disinfectants, contain antimicrobial agents which are not naturally occurring. Typical antimicrobial agents used in sanitizers and disinfectants include chemical disinfectants such as phenolic compounds, quaternary ammonium compounds, formaldehyde and halogen containing compounds. Such materials are not of natural origin (i.e. not found in nature) and are prepared through chemical processing and synthesis. A great many of these "synthetic" disinfectants cause undesirable effects on both the environment and on human health. The concept of formulating disinfectants, essentially involving the selection of a simple chemical disinfectant and enhancing its activity by adding other chemicals, evolved in the seventies.

The enhancement of the activity of a simple chemical disinfectant or combination of simple disinfectants to increase the spectrum of activity frequently involves the addition of additional chemical agents. Such additional chemical agents will generally have an effect on the pH and surface activity of the formulated product once in solution. It is well established that a number of simple disinfectants demonstrate their optimum activity at a specific pH (i.e. acidity or alkalinity). The ability of the disinfectant solution to make complete and even contact with the surface to be treated is also of great importance. This can generally be achieved by the addition of a surfactant or detergent to the formulation.

Disinfectants play a vital role in any biosecurity system, both in the process of terminal disinfection and in the ongoing hygiene maintenance. Apart from relatively minor changes and improvements in formulations, there has been little innovation in livestock disinfectant and large-surface disinfectant development for some fifteen to twenty years.

While some natural plant oils have been known since antiquity to have curative properties, the topical and oral benefits of natural plant oils have more recently been attributed to antimicrobial properties. A great many of the natural essential oils are derived from cajeput, cedarwood, citronella, clove, cypress, fir-needle, eucalyptus, garlic, lavender, lemon, lemongrass, marjoram, niaouli, onion, orange, oregano, patchouli, peppermint, rosemary, rosewood, tea tree, y-lang and vetivert. Of these natural essential oils, oregano oil, comprising a complex mixture of antimicrobial compounds, has been used as a reference for the comparison of the bactericidal action of other substances owing to its near ideal antibacterial properties. Oregano oil has been demonstrated as exerting a high degree of anti-fungal, anti-parasitic, antiviral and antibacterial action. The phenolic flavenoids carvacol and thymol are two potent natural antiseptic agents encountered primarily in oregano oil.

Attempts have been made to formulate disinfectant solutions based upon essential oils. However, because of their hydrophobic nature, essential oils are not readily miscible in water. As a result, essential oils are often difficult to prepare in a form that will allow them to be readily incorporated into an aqueous solution.

U.S. Pat. No. 5,403,587 issued to McCue et al. on Apr. 4, 1995 discloses an antimicrobial composition that uses both a solvent and a surfactant to facilitate the formation of a homogeneous aqueous mixture of an essential oil. However, this composition is not suitable for disinfecting large surfaces such as commonly encountered in agricultural settings where the disinfectant solution is commonly prepared from a concentrate using the on-site water source.

The present invention refers to a number of documents, the content of which is herein incorporated by reference in their entirety.

SUMMARY OF THE INVENTION

The present invention relates to disinfectant formulations comprising one or more phenolic compounds of natural origin.

As broadly claimed, the present invention relates to aqueous formulations suitable for disinfecting and cleaning large surfaces and comprising one or more phenolic compounds of natural origin.

In an embodiment, the present invention relates to an aqueous disinfectant formulation comprising:

at least one phenolic compound of natural origin;
a surfactant sufficient to form a solution or dispersion of the phenolic compound in an aqueous carrier;
a solvent;
a sequestering agent; and
sufficient water to make 100 weight percent.

In an embodiment, the present invention relates to an aqueous disinfectant formulation comprising:

at least one phenolic compound of natural origin;
a surfactant sufficient to form a solution or dispersion of the phenolic compound in an aqueous carrier;
a solvent; and
sufficient water to make 100 weight percent.

In an embodiment of the present invention, the phenolic compound of natural origin is an active ingredient commonly found in essential oils. In a further embodiment of the present invention, the phenolic compound is an active ingredient of oregano oil.

In an embodiment, the present invention relates to disinfectant formulations exhibiting antibacterial properties.

In an embodiment, the present invention relates to disinfectant formulations exhibiting antimicrobial properties.

In an embodiment, the present invention relates to an aqueous disinfectant formulation for denaturing biofilms.

In an embodiment, the present invention relates to disinfectant formulations exhibiting antiviral properties.

In an embodiment, the present invention relates to disinfectant formulations exhibiting antifungal properties.

In an embodiment, the present invention relates to a disinfectant formulation comprising a homogeneous aqueous solution.

In an embodiment, the present invention relates to an aqueous disinfectant formulation generating a foam when applied to a surface to be disinfected. The foam adheres to the surface to be disinfected for a time sufficient to ensure eradication of the non-indigenous and/or pathogenic bacterial population.

In an embodiment, the present invention relates to an aqueous disinfectant formulation generating a foam when applied to a surface to be disinfected. The foam adheres to the surface to be disinfected for a time sufficient to ensure eradication of the non-indigenous and/or pathogenic microbial population.

In an embodiment, the present invention relates to an aqueous disinfectant formulation generating a foam when applied to a surface to be disinfected. The foam adheres to the surface to be disinfected for a time sufficient to ensure eradication of the non-indigenous pathogenic and/or viral population.

In an embodiment, the present invention relates to an aqueous disinfectant formulation generating a foam when applied to a surface to be disinfected. The foam adheres to the surface to be disinfected for a time sufficient to ensure eradication of the non-indigenous and/or pathogenic fungal population.

The disinfectant formulations of the present invention can be dispensed using any suitable application means. In an embodiment, the disinfectant formulations of the present invention are applied to a surface using a foamer.

In a further embodiment, the present invention relates to biodegradable disinfectant formulations.

The present invention also relates to disinfectant formulations retaining their properties when diluted with hard water.

The formulations of the present invention and methods for their use can "comprise," "consist essentially of," or "consist of" any of the ingredients disclosed throughout the specification.

The foregoing and other objects, advantages and features of the present disclosure will become more apparent upon reading of the following non restrictive description of illustrative embodiments thereof, given by way of example only.

DETAILED DESCRIPTION OF ILLUSTRATIVE EMBODIMENTS

In order to provide a clear and consistent understanding of the terms used in the present specification, a number of definitions are provided below. Moreover, unless defined otherwise, all technical and scientific terms as used herein have the same meaning as commonly understood to one of ordinary skill in the art to which this invention pertains.

The use of the word "a" or "an" when used in conjunction with the term "comprising" in the claims and/or the specification may mean "one", but it is also consistent with the meaning of "one or more", "at least one", and "one or more than one". Similarly, the word "another" may mean at least a second or more.

As used in this specification and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

The term "about" is used to indicate that a value includes an inherent variation of error for the device or the method being employed to determine the value.

The term "hard water" as used herein refers to water having a high concentration of dissolved minerals and solids.

The term "natural origin" as used herein refers to phenolic compounds that exist or are produced in nature. Such phenolic compounds can be extracted or isolated from their natural environment by any suitable means. Of course, such phenolic compounds can also be synthetically produced by the hand of man. Such synthetic equivalents are within the definition of "natural origin".

Antimicrobial agents that are useful in the present invention are the so-called "natural" antimicrobial actives, referred to as natural essential oils. These actives derive their names from their natural occurrence in plants. Essential oils include oils derived from herbs, flowers, trees, and other plants. Such oils are typically present as tiny droplets between the plant's cells, and can be extracted by several methods known to those of skill in the art (e.g., steam distillation, enfleurage (i.e., extraction using fat(s)), maceration, solvent extraction, or mechanical pressing). Essential oils are typically named by the plant or vegetable in which the oil is found. For example, rose oil or peppermint oil is derived from rose or peppermint plants, respectively. Non-limiting examples of essential oils that can be used in the context of the present invention include oils of anise, lemon oil, orange oil, oregano, rosemary oil, wintergreen oil, thyme oil, lavender oil, clove oil, hops, tea tree oil, citronella oil, wheat oil, barley oil, lemongrass oil, cedar leaf oil, cedar wood oil, cinnamon oil, fleagrass oil, geranium oil, sandalwood oil, violet oil, cranberry oil, eucalyptus oil, vervain oil, peppermint oil, gum benzoin, basil oil, fennel oil, fir oil, balsam oil, menthol, ocmea *origanum* oil, *Hydastis carradensis* oil, *Berberidaceae daceae* oil, Ratanhiae and *Curcuma longa* oil, sesame oil, *macadamia* nut oil, evening primrose oil, Spanish sage oil, Spanish rosemary oil, coriander oil, thyme oil, pimento berries oil, rose oil, bergamot oil, rosewood oil, chamomile oil, sage oil, clary sage oil, cypress oil, sea fennel oil, frankincense oil, ginger oil, grapefruit oil, jasmine oil, juniper oil, lime oil, mandarin oil, marjoram oil, myrrh oil, neroli oil, patchouli oil, pepper oil, black pepper oil, petitgrain oil, pine oil, rose otto oil, spearmint oil, spikenard oil, vetiver oil, or ylang ylang. Other essential oils known to those of skill in the art are also contemplated as being useful within the context of the present invention (e.g., International Cosmetic Ingredient Dictionary, $10^{th}$ and $12^{th}$ editions, 2004 and 2008, respectively, which are incorporated by reference). Also included in this class of essential oils are the key chemical components of the plant oils that have been found to provide the antimicrobial benefit (e.g. phenolic compounds).

The phenolic compounds of natural origin as used in the present invention can be synthetically made by known methods within the capacity of a skilled technician, or can be obtained from plant oil extracts. In an embodiment of the present invention, the phenolic compounds of natural origin are obtained from plant extracts. In a further embodiment of the present invention, the phenolic compounds of natural origin are commercially available. In yet a further embodiment of the present invention, the phenolic compounds of natural origin comprise carvacrol and thymol.

In an embodiment, the disinfectant formulations of the present invention comprise thymol, carvacrol or mixtures thereof. In a further embodiment, the disinfectant formulations of the present invention comprise one or more natural essential oils enriched in thymol, carvacrol or mixtures of thymol and carvacrol.

In an embodiment, the disinfectant formulations of the present invention further comprise a surfactant. A surfactant operative herein comprises a water soluble or water dispersible nonionic, anionic, cationic, or an amphoteric compound. In a further embodiment, the disinfectant formulations of the present invention comprise one or more of the conventional anionic surfactants known in the art. A representative listing of surfactants and properties thereof is detailed in Remington's Pharmaceutical Sciences, $17^{th}$ edition (Mack Publishing Company). Non-limiting examples of surfactants according to an embodiment of the present invention include sodium lauryl sulfate, sorbitan stearate, sorbitan esters, sodium laureth sulfate, sarkosyl, cocamidopropyl betaine (CAPB), sodium lauryl ether sulfonate, alkyl benzene sulfonates, nonylphenol ethoxylate and ether ethoxylate. It is appreciated that one or more additional surfactants may be included in the disinfectant formulations of the present invention. A surfactant (surface active agent) is generally intended to refer to a substance which when dissolved in water, or other aqueous system, reduces the surface or interfacial tension between it and another substance or material. In an embodiment of the present invention, the surfactant aids in the dispersion or emulsification of the essential oils within the aqueous carrier. In a further embodiment of the present invention, the anionic surfactant aids in braking down the structure of biofilms through denaturation. In yet a further embodiment of the present invention, the surfactant allows for the creation of a "foaming effect" when the disinfectant solution is applied to a surface to be treated. The creation of a foam allows for the disinfectant solutions to remain in contact with the surface to be treated for longer periods of time. In yet a further embodiment, the surfactant acts as a "wetting" agent. Wetting agents typically reduce the surface tension of the water molecules, allowing for a greater spreading of the solution and a deeper penetration into small crack and crevices of the surface to be treated.

Phenolic compounds (e.g. carvacrol, thymol) are typically not sufficiently soluble in an aqueous medium. The disinfectant formulations of the present invention thus typically comprise a solvent. The solvents may be hydrophilic, hydrophobic or amphiphilic in nature. In an embodiment, the disinfectant formulations of the present invention comprise an amphiphilic solvent. Amphiphilic solvents are capable of solubilizing the phenolic compounds of natural origin and/or the essential oil(s) in the aqueous carrier. Non-limiting examples of solvents according to an embodiment of the present invention include methanol, ethanol, hexadecane, propylene glycol, propylene glycol n-butyl ether, propylene glycol methyl ether acetate, propylene glycol methyl ether, dipropylene glycol n-propyl ether, ethylene glycol methyl ether and hexylene glycol. The addition of a significant amount of solvent to the disinfectant solutions of the present invention, allows for the solutions to be used at temperatures slightly inferior to 0° C. It is well within the capacity of a skilled technician to determine such amounts of solvent.

Since the disinfectant formulations are typically prepared on site from mixtures of ingredients in concentrated solution, tap water is used for dilution. Tap water generally has a certain amount of hardness. Since the presence of dissolved minerals (e.g. $Ca^{++}$, $Mg^{++}$) may adversely affect the performance and properties of the disinfectant formulation, a sequestering agent is included in the formulation to chelate the dissolved minerals in the form of a water soluble complex. Sequestering agents are well known in the art. Non-limiting examples include ethylene diamine tetraacetic acid (EDTA) sodium salt, sodium gluconate, sodium citrate, trisodium ethylenediamine disuccinate, citric acid, trisodium NTA, sodium phosphate and sodium choleate. Sequestering agents typically prevent the dissolved minerals from binding to the surfactant molecules. Moreover, sequestering agents may remove minerals from the surface to be disinfected.

In an embodiment, the disinfectant formulations of the present invention comprise one or more phenolic compounds of natural origin. In an embodiment of the present invention, the phenolic compounds are selected from the group consisting of thymol and carvacrol. In a further embodiment, the disinfectant formulations of the present invention comprise carvacrol. In a further embodiment, the disinfectant formulations of the present invention comprise thymol. In a further embodiment, the disinfectant formulations of the present invention comprise carvacrol and thymol. In a particular embodiment, the disinfectant formulations of the present invention comprise 0.18% (w/w) thymol.

Phenolic compounds typically have an associated pungent odor severely impeding large-scale applications. In an embodiment, the disinfectant formulations of the present invention may thus further comprise one or more agents having the dual function of further enhancing the disinfectant properties of the formulations while imparting a more pleasant odor thereto. In yet a further embodiment of the present invention, the disinfectant formulations of the present invention may further comprise one or more agents imparting a pleasant odor thereto (fragrance agent). Non-limiting examples of agents imparting a pleasant odor and/or enhancing the disinfectant properties comprise carvacrol, cymene, cineol, eugenol, thymol, menthol, citral and limonene. Further suitable examples of such agents are within the capacity of a skilled technician.

The disinfectant formulations of the present invention may optionally include a wide range of additional ingredients non-limiting examples of which include colorants and pH adjusting agents. Such additional ingredients are within the capacity of a skilled technician.

The disinfectant formulations of the present invention may be applied onto a surface to be disinfected (i.e. cleaned) by means of a variety of spraying techniques. In an embodiment, the disinfectant formulations of the present invention are applied using a diffuser or a mist blower. Alternatively, the disinfectant formulations of the present invention can also be formulated into aerosol formulations. Further means of applying the disinfectant solutions of the present invention are within the capacity of a skilled technician. The disinfectant formulations of the present invention can either be applied directly or can be diluted prior to application. Due to the substantially non-corrosive nature of the disinfectant formulations of the present invention, the formulations can be readily applied without undue damage to the existing physical structure (i.e. surface).

In an embodiment, the disinfectant formulations of the present invention comprise one or more essential oils enriched in thymol and/or carvacrol. Thymol and carvacrol are naturally occurring disinfectants which are readily degraded in the environment. As such, there is little or no accumulation in the environment or in living organisms, even following repeated application of the disinfectant formulations of the present invention.

Formulations of the present invention can include any number of combinations of ingredients discussed throughout this specification (e.g., phenolic compounds of natural origin, essential oils, surfactants, solvents, sequestering agents, water, etc.). It is also contemplated that that the concentrations of the ingredients can vary. In non-limiting embodiments, for example, the formulations may include in their final form, for example, at least about 0.0001%, 0.0002%, 0.0003%, 0.0004%, 0.0005%, 0.0006%, 0.0007%, 0.0008%, 0.0009%, 0.0010%, 0.0011%, 0.0012%, 0.0013%, 0.0014%, 0.0015%, 0.0016%, 0.0017%, 0.0018%, 0.0019%, 0.0020%, 0.0021%, 0.0022%, 0.0023%, 0.0024%, 0.0025%, 0.0026%, 0.0027%, 0.0028%, 0.0029%, 0.0030%, 0.0031%, 0.0032%, 0.0033%, 0.0034%, 0.0035%, 0.0036%, 0.0037%, 0.0038%, 0.0039%, 0.0040%, 0.0041%, 0.0042%, 0.0043%, 0.0044%, 0.0045%, 0.0046%, 0.0047%, 0.0048%, 0.0049%, 0.0050%, 0.0051%, 0.0052%, 0.0053%, 0.0054%, 0.0055%, 0.0056%, 0.0057%, 0.0058%, 0.0059%, 0.0060%, 0.0061%, 0.0062%, 0.0063%, 0.0064%, 0.0065%, 0.0066%, 0.0067%, 0.0068%, 0.0069%, 0.0070%, 0.0071%, 0.0072%, 0.0073%, 0.0074%, 0.0075%, 0.0076%, 0.0077%, 0.0078%, 0.0079%, 0.0080%, 0.0081%, 0.0082%, 0.0083%, 0.0084%, 0.0085%, 0.0086%, 0.0087%, 0.0088%, 0.0089%, 0.0090%, 0.0091%, 0.0092%, 0.0093%, 0.0094%, 0.0095%, 0.0096%, 0.0097%, 0.0098%, 0.0099%, 0.0100%, 0.0200%, 0.0250%, 0.0275%, 0.0300%, 0.0325%, 0.0350%, 0.0375%, 0.0400%, 0.0425%, 0.0450%, 0.0475%, 0.0500%, 0.0525%, 0.0550%, 0.0575%, 0.0600%, 0.0625%, 0.0650%, 0.0675%, 0.0700%, 0.0725%, 0.0750%, 0.0775%, 0.0800%, 0.0825%, 0.0850%, 0.0875%, 0.0900%, 0.0925%, 0.0950%, 0.0975%, 0.1000%, 0.1250%, 0.1500%, 0.1750%, 0.2000%, 0.2250%, 0.2500%, 0.2750%, 0.3000%, 0.3250%, 0.3500%, 0.3750%, 0.4000%, 0.4250%, 0.4500%, 0.4750%, 0.5000%, 0.5250%, 0.0550%, 0.5750%, 0.6000%, 0.6250%, 0.6500%, 0.6750%, 0.7000%, 0.7250%, 0.7500%, 0.7750%, 0.8000%, 0.8250%, 0.8500%, 0.8750%, 0.9000%, 0.9250%, 0.9500%, 0.9750%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 65%, 70%, 75%, 80%, 85%, 90%, 95%, or 99% or more, or any range or integer derivable therein, of at least one of the ingredients mentioned throughout the specification and/or claims. In non-limiting aspects, the percentage can be calculated by weight or volume of the total composition. A person of ordinary skill in the art would understand that the concentrations can vary depending on the desired effect of the formulation and/or on the product into which the formulation is incorporated into.

EXPERIMENTAL

Disinfectant Solutions

Chemical and Physical Characteristics of the Disinfectant Solutions

The sequestering agent (sodium citrate) was first dissolved in a predetermined amount of water and stirred until dissolution. Glycol ether PM (solvent), thymol, *origanum* oil and optionally citral (fragrance) were then added and stirred until dissolution. Surfactant (Sodium Lauryl Sulfate) and additional water were then added and stirred until dissolution to provide a 100 wt. % formulation. The final formulation was stirred until a homogeneous solution was obtained. Formulation 1, obtained from Formulation 2 by means of dilution with water (1:100), is considered a "ready to use" formulation.

|   | Thymol Crystal | Origanum Oil/Citral | Sequestrant | Surfactant | Solvent | pH |
|---|---|---|---|---|---|---|
| A | 0.18 | 0.04 | 0.01 | 0.12 | — | 6.9 |
| B | 0.18 | 0.04 | 0.01 | — | 0.18 | 6.7 |
| C | 0.18 | 0.04 | — | 0.12 | 0.18 | 6.5 |
| 1 | 0.18 | 0.04 | 0.01 | 0.12 | 0.18 | 6.5 |
| D | 18 | 4 | 1 | 12 | — | 8.1 |
| E | 18 | 4 | 1 | — | 18 | 7.9 |
| 2 | 18 | 4 | 1 | 12 | 18 | 8.8 |
| 3 | 0.18 | 0.03 | 0.09 | 0.12 | 0.76 | 8.0 |
| 4 | 6 | 1 | 3 | 4 | 25 | 8.2 |

|   | Solubility in Water | Stability | Foaming Effect | Foaming Effect in Hard Water |
|---|---|---|---|---|
| A | NO | NO | YES | YES |
| B | NO | NO | NO | YES |
| C | YES | YES | YES | NO |
| 1 | YES | YES | YES | YES |
| D | NO | NO | YES | n/a |
| E | NO | NO | NO | n/a |
| 2 | YES | YES | YES | n/a |
| 3 | YES | YES | YES | YES |
| 4 | YES | YES | YES | n/a | n/a: Not applicable this formula requires dilution before use

As illustrated hereinabove, the formulations are first formulated as a "concentrate" (Formulations 2 and 4), dilution of which provides for the preparation of Formulations 1 and 3. Formulations A, B, C, D, E, 1 and 2 comprise *Origanum* Oil/Citral (3:1). Formulations 3 and 4 do not comprise any fragrance (citral). The formulations have a pH ranging from about 6 to about 9. Dilution using hard water did not affect the characteristics of the formulation which is indicative of the efficacy of the sequestering agent.

Biological Efficacy of Selected Phenolic Compounds and Essential Oils

The minimum concentration at which a total antimicrobial activity could be observed was determined for selected phenolic compounds of natural origin and selected essential oils using the AOAC method 955.15 ("Phenol Coefficient Method") with minor modifications. The results are indicative of the excellent antimicrobial activity of both thymol and carvacrol.

| Antimicrobial Agent | Minimal Concentration (v/v %) |
|---|---|
| Thymol | 0.07 |
| Carvacrol | 0.07 |
| Eugenol | 0.4 |
| Citral | >1% |
| Thyme oil | 0.3 |
| *Origanum* oil | 0.2 |
| *Eucalyptus* oil | >1% |
| Lemon oil | >1% |

Different concentrations of essential oils and phenolic compounds of natural origin were incorporated into composition F (see table hereinbelow) and inoculated with a 0.05% bacterial suspension of *Staphylococcus aureus* (ATCC 6538; concentration of about 8 logs). After a contact time of 10 minutes, 0.1 ml of the inoculated solution was transferred to a broth culture with neutralizing (Difco 268110) and incubated over a period of 72 hours at 37° C. The presence of turbidity in the broth culture is indicative of the survival of the microorganism.

Quantitative Microbial Reduction Assay

The antimicrobial activity for selected formulations of the present invention was determined. Several formulations comprising a phenolic compound of natural origin or an essential oil (0.18%) were tested to determine their effectiveness in reducing the load of *Staphylococcus aureus* (ATCC 6538). The solutions were prepared from a concentrate and diluted with water (1:100). The results are indicative of the high efficiency of Formulations 5, 6 and 7 in reducing the load of *Staphylococcus aureus*.

| | Antimicrobial Agent (w/w) | Sequestrant (w/w) | Surfactant (w/w) | Solvent (w/w) | Log Reduction |
|---|---|---|---|---|---|
| F | — | 0.01 | 0.12 | 0.18 | 0.60 |
| 5 | Thymol | 0.01 | 0.12 | 0.18 | 7.63 |
| 6 | Carvacrol | 0.01 | 0.12 | 0.18 | 7.63 |
| G | Eugenol | 0.01 | 0.12 | 0.18 | 2.50 |
| H | Citral | 0.01 | 0.12 | 0.18 | 2.04 |
| I | Thyme oil | 0.01 | 0.12 | 0.18 | 3.06 |
| 7 | Origanum oil | 0.01 | 0.12 | 0.18 | 7.63 |
| J | Eucalyptus oil | 0.01 | 0.12 | 0.18 | 0.71 |
| K | Lemon oil | 0.01 | 0.12 | 0.18 | 0.64 |

Different formulations of the present invention were inoculated with 0.05% of a bacterial culture of *Staphylococcus aureus* (ATCC 6538) freshly incubated over a period of 48 hours at 37° C. in an optimal growth medium. After a contact time of 10 minutes, 0.1 ml of the inoculated solution was seeded at different dilutions on TSA agar (Difco 255320) with neutralizing to determine the residual microbial load. The log reduction was determined by calculating the logarithm of the residual charge obtained with the reference formulation (i.e. water) and comparing it with the residual charge obtained using any of the formulations comprising either a phenolic compound or an essential oil.

Biological Efficacy of Formulation 1 on Selected Microorganisms

The disinfectant formulations of the present invention exhibit a broad spectrum of activity on a variety of microorganisms. As shown hereinbelow, the efficacy of Formulation 1 against a variety of microorganisms was determined.

| Activity | Standard Method | Group of Microorganisms | Microorganism | 1 |
|---|---|---|---|---|
| Bactericidal | AOAC[1] (Dilution Test) | Bacteria Gram− | *Salmonella cholerasuis* | Pass |
| | | Bacteria Gram+ | *Staphylococcus aureus* | Pass |
| Fungicide | AOAC Fungicidal Activity Test | Fungus | *Trichophyton mentagrophytes* | Pass |
| Virucidal | ASTM[2] Efficacy of Virucidal Agents | Virus | Influenza A | Pass |

[1]Association of Analytical Communities,
[2]American Society for Testing and Materials Toxicity of the Disinfectant Formulations Toxicity tests ($LD_{50}$) were performed on selected ingredients of the disinfectant formulations of the present invention. Formulation 1 was determined as having a $LD_{50}$ of >15 g/Kg (substantially non-toxic).

| Ingredient | $LD_{50}$ Oral-rat | Specification |
|---|---|---|
| Thymol | 980 mg/kg | USP, FCC |
| Origanum oil | 1850 mg/kg | USP, FCC |
| Citral | 4960 mg/kg | Oxford University |
| Sodium Citrate | >8 g/kg | USP, FCC |
| Sodium Lauryl Sulfate | 1288 mg/kg | USP, FCC |
| Glycol Ether PM | 5210 mg/kg | WHMIS |

It is to be understood that the invention is not limited in its application to the details of construction and parts as described hereinabove. The invention is capable of other embodiments and of being practiced in various ways. It is also understood that the phraseology or terminology used herein is for the purpose of description and not limitation. Hence, although the present invention has been described hereinabove by way of illustrative embodiments thereof, it can be modified, without departing from the spirit, scope and nature of the subject invention as defined in the appended claims.

The invention claimed is:

1. An aqueous disinfectant formulation consisting of:
   a) from about 0.05% to about 25% weight of at least one antimicrobial isolated or synthetic phenolic compound of natural origin selected from the group consisting of thymol and carvacrol;
   b) from about 0.1% to about 15% weight of a surfactant sufficient to form a solution or dispersion of said phenolic compound in an aqueous carrier, consisting of sodium lauryl sulfate;

c) from about 0.1% to about 40% weight of a solvent;
d) from about 0.01% to about 10% weight of a sequestering agent selected from the group consisting of ethylene diamine tetraacetic acid (EDTA) sodium salt, sodium gluconate, citric acid, trisodium NTA, trisodium ethylene disuccinate, and sodium choleate; and
e) sufficient water to make 100 weight percent.

2. The aqueous disinfectant formulation of claim 1, wherein said solution consists of:
a) from about 5% to about 25% weight percent of said phenolic compound;
b) from about 5% to about 15% weight percent of said surfactant;
c) from about 5% to about 35% weight of said solvent; and
d) from about 1% to about 5% weight percent of said sequestering agent; and
e) sufficient water to make 100 weight percent.

3. The aqueous disinfectant formulation of claim 1, wherein said solution consists of:
a) from about 15% to about 25% weight of said phenolic compound;
b) from about 10% to about 15% weight of said surfactant;
c) from about 15% to about 30% weight of said solvent; and
d) from about 1% to about 3% weight percent of said sequestering agent; and
e) sufficient water to make 100 weight percent.

4. The aqueous disinfectant formulation of claim 1, comprising a pH ranging from about 6 to about 9.

5. A method of using the disinfectant formulation of claim 1, comprising the step of diluting the disinfectant formulation with water.

6. A method of disinfecting a surface comprising applying the disinfectant formulation of claim 1 to a surface in need of disinfecting.

7. A method of disinfecting a surface in accordance with claim 6, wherein said disinfecting formulation is applied neat or in diluted form.

8. An aqueous disinfectant formulation consisting of:
a) from about 0.05% to about 25% weight of at least one antimicrobial isolated or synthetic phenolic compound of natural origin selected from the group consisting of thymol and carvacrol;
b) from about 0.1% to about 15% weight of a surfactant sufficient to form a solution or dispersion of said phenolic compound in an aqueous carrier, consisting of sodium lauryl sulfate;
c) from about 0.1% to about 40% weight of a solvent;
d) from about 0.01% to about 10% weight of a sequestering agent selected from the group consisting of ethylene diamine tetraacetic acid (EDTA) sodium salt, sodium gluconate, citric acid, trisodium NTA, trisodium ethylene disuccinate, and sodium choleate;
e) from about 0.04% to about 4% weight of an essential oil is selected from the group consisting of *origanum* oil, thyme oil, and eucalyptus oil, and
f) sufficient water to make 100 weight percent.

9. The aqueous disinfectant formulation of claim 8, wherein said solution consists of:
a) from about 5% to about 25% weight percent of said phenolic compound;
b) from about 5% to about 15% weight percent of said surfactant;
c) from about 5% to about 35% weight of said solvent; and
d) from about 1% to about 5% weight percent of said sequestering agent;
e) from about 0.04% to about 4% weight of said essential oil; and
f) sufficient water to make 100 weight percent.

10. The aqueous disinfectant formulation of claim 8, wherein said solution consists of:
a) from about 15% to about 25% weight of said phenolic compound;
b) from about 10% to about 15% weight of said surfactant; and
c) from about 15% to about 30% weight of said solvent; and
d) from about 1% to about 3% weight percent of said sequestering agent;
e) from about 0.04% to about 4% weight of said essential oil; and
f) sufficient water to make 100 weight percent.

11. The aqueous disinfectant formulation of claim 8, comprising a pH ranging from about 6 to about 9.

12. A method of using the disinfectant formulation of claim 8, comprising the step of diluting the disinfectant formulation with water.

13. A method of disinfecting a surface comprising applying the disinfectant formulation of claim 8 to a surface in need disinfecting.

14. A method of disinfecting a surface in accordance with claim 13, wherein said disinfecting formulation is applied neat or in diluted form.

15. An aqueous disinfectant formulation consisting of:
a) from about 0.05% to about 25% weight of at least one antimicrobial isolated or synthetic phenolic compound of natural origin selected from the group consisting of thymol and carvacrol;
b) from about 0.1% to about 15% weight of a surfactant sufficient to form a solution or dispersion of said phenolic compound in an aqueous carrier, consisting of sodium lauryl sulfate;
c) from about 0.1% to about 40% weight of a solvent;
d) from about 0.01% to about 10% weight of a sequestering agent selected from the group consisting of ethylene diamine tetraacetic acid (EDTA) sodium salt, sodium gluconate, citric acid, trisodium NTA, trisodium ethylene disuccinate, and sodium choleate;
e) a fragrance; and
f) sufficient water to make 100 weight percent.

16. The aqueous disinfectant formulation of claim 15, wherein said solution consists of:
a) from about 5% to about 25% weight of said phenolic compound;
b) from about 5% to about 15% weight of said surfactant;
c) from about 5% to about 35% weight of said solvent; and
d) from about 1% to about 5% weight percent of said sequestering agent; and
e) from about 0.04% to about 1.5% weight of said fragrance; and
f) sufficient water to make 100 weight percent.

17. The aqueous disinfectant formulation of claim 15, wherein said solution consists of:
a) from about 15% to about 25% weight percent of said phenolic compound;
b) from about 10% to about 15% weight percent of said surfactant;
c) from about 15% to about 30% weight of said solvent; and
d) from about 1% to about 3% weight percent of said sequestering agent; and
e) from about 0.04% to about 1.5% weight of said fragrance; and f) sufficient water to make 100 weight percent.

18. An aqueous disinfectant formulation consisting of:
   a) from about 0.05% to about 25% weight of at least one antimicrobial isolated or synthetic phenolic compound of natural origin selected from the group consisting of thymol and carvacrol;
   b) from about 0.1% to about 15% weight of a surfactant sufficient to form a solution or dispersion of said phenolic compound in an aqueous carrier, consisting of sodium lauryl sulfate;
   c) from about 0.1% to about 40% weight of a solvent;
   d) from about 0.01% to about 10% weight of a sequestering agent selected from the group consisting of ethylene diamine tetraacetic acid (EDTA) sodium salt, sodium gluconate, citric acid, trisodium NTA, trisodium ethylene disuccinate, and sodium choleate;
   e) a fragrance;
   f) from about 0.04% to about 4% weight of an essential oil is selected from the group consisting of *origanum* oil, thyme oil, and eucalyptus oil, and
   g) sufficient water to make 100 weight percent.

19. The aqueous disinfectant formulation of claim 18, wherein said solution consists of:
   a) from about 5% to about 25% weight of said phenolic compound;
   b) from about 5% to about 15% weight of said surfactant;
   c) from about 5% to about 35% weight of said solvent; and
   d) from about 1% to about 5% weight percent of said sequestering agent;
   e) from about 0.01% to about 1.5% weight of said fragrance;
   f) from about 0.04% to about 4% weight of said essential oil; and
   g) sufficient water to make 100 weight percent.

20. The aqueous disinfectant formulation of claim 18, wherein said solution consists of:
   a) from about 15% to about 25% weight of said phenolic compound;
   b) from about 10% to about 15% weight of said surfactant;
   c) from about 15% to about 30% weight of said solvent; and
   d) from about 1% to about 3% weight percent of said sequestering agent;
   e) from about 0.04% to about 1.5% weight of said fragrance;
   f) from about 0.04% to about 4% weight of said essential oil; and
   g) sufficient water to make 100 weight percent.

* * * * *